US00PP28170P3

(12) United States Plant Patent
Olesen

(10) Patent No.: US PP28,170 P3
(45) Date of Patent: Jul. 11, 2017

(54) COMPACT FLORIBUNDA ROSE PLANT NAMED 'POULPAL066'

(50) Latin Name: ***Rosa* hybrid**
Varietal Denomination: Poulpal066

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 14 days.

(21) Appl. No.: 14/756,256

(22) Filed: Aug. 20, 2015

(65) Prior Publication Data

US 2017/0055406 P1 Feb. 23, 2017

(51) Int. Cl.
*A01H 5/02* (2006.01)

(52) U.S. Cl.
USPC ..... Plt./151

(58) Field of Classification Search
USPC ..... Plt./141, 151
See application file for complete search history.

(56) References Cited

PUBLICATIONS

Poulsen Roser A/S "Palace-Perfection by Poulsen" Oct. 2012 (1 page).*

* cited by examiner

*Primary Examiner* — Susan McCormick Ewoldt

(57) ABSTRACT

A new garden rose plant of the Compact Floribunda class which has abundant, red flowers and attractive foliage. This new and distinct variety has shown to be uniform and stable in the resulting generations from asexual propagation.

2 Drawing Sheets

Botanical designation: *Rosa* hybrid.
Variety denomination: 'Poulpal066'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulpal066', originated as a single seedling from the stated cross.

The new variety may be distinguished from its male pollen parent and female seed parent primarily by the following characteristics. The female seed parent has medium pink flowers while the new variety has red flowers. The male pollen parent has flowers which are 70 mm in diameter, while the new variety has flowers which are 90 mm in diameter.

The objective of the hybridization of this rose variety was to create a new and distinct variety for garden use with unique qualities, such as:

1. Uniform and abundant red flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpal066' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulpal066' was selected in the spring of 2009 by the inventor as a single plant from the progeny of the aforementioned hybridization.

Asexual reproduction of 'Poulpal066' by traditional budding and rooted cuttings was first done by Mogens N. Olesen in the nursery in Fredensborg, Denmark in July, 2009. This initial and other subsequent asexual propagations conducted in controlled environments have demonstrated that the characteristics of 'Poulpal066' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpal066'.

Specifically illustrated in FIG. 1 of the drawings are open flowers, flower petals detached, sepals detached, reproductive flower parts, and flower buds.

Figure 1:
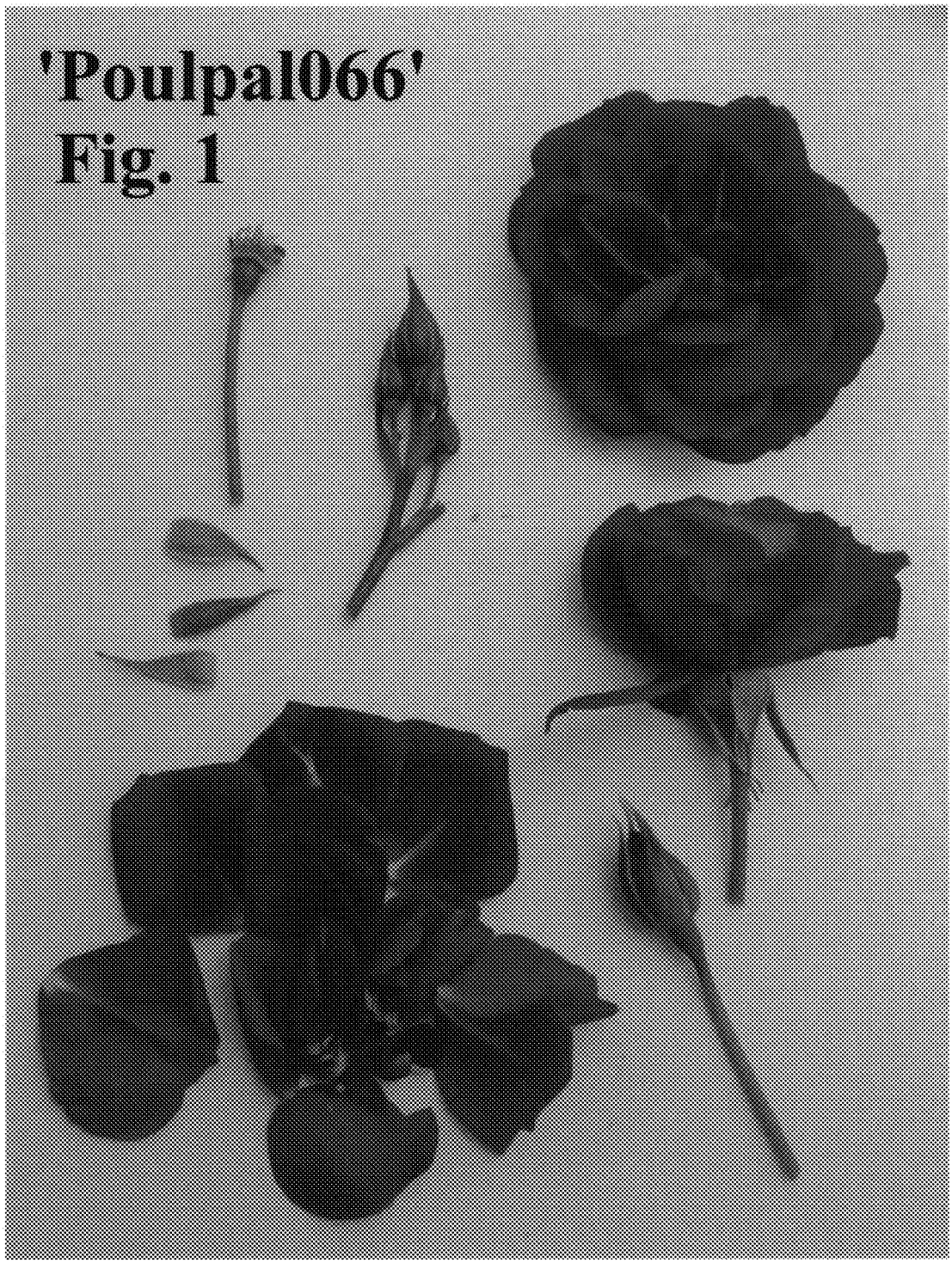
Figure 2:
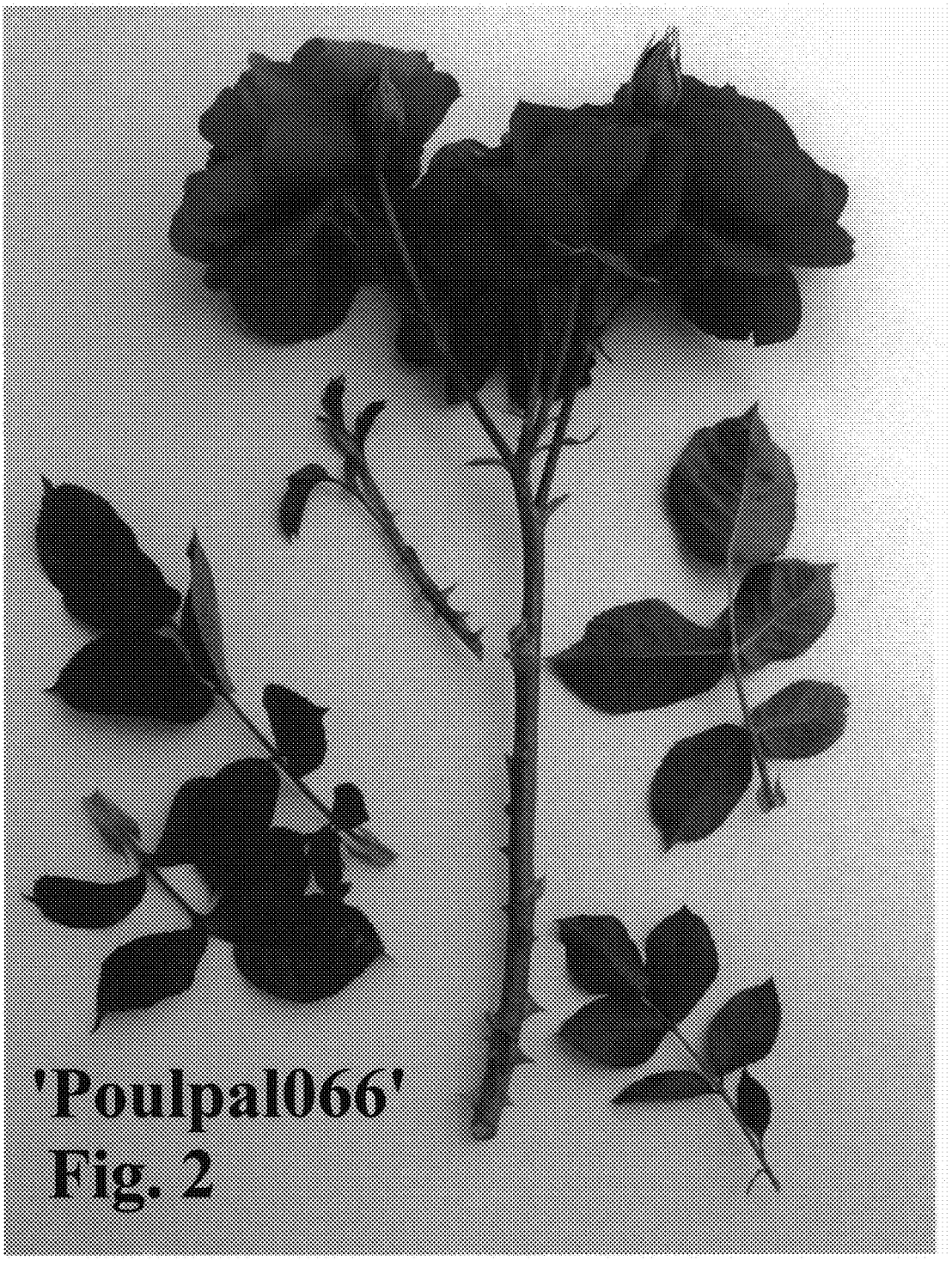

Specifically illustrated in FIG. 2 of the drawings are a cluster of open flowers on a bare branch, juvenile stem, juvenile leaves, and mature leaves.

Plants shown are 2 years of age.

DETAILED DESCRIPTION OF THE VARIETY

The following is a description of 'Poulpal066', as observed in its growth in in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulgrad', U.S. Plant Pat. No. 11,610 are compared to 'Poulpal066' in Chart 1.

CHART 1

| | 'Poulpal066' | 'Poulgrad' |
|---|---|---|
| Petal Count | 50 petals | 25-30 |
| Flower Diameter | 90 mm | 55 mm |
| General Tonality of Flower Color | Red-Purple Group 50A blended with Red-Purple Group 60B | Red Group 53A-46A |

Flower and Flower Bud

Blooming habit: Continuous.

Flower bud:

*Size.*—Upon opening, 33 mm in length from base of receptacle to end of bud. Bud diameter is 15 mm.

*Bud form.*—Ovoid.

*Bud color.*—As sepals divide petals are Red Group 46A.

*Sepal inner surface.*—Color: Yellow-Green Group 147C. Surface: Lightly pubescent.

*Sepal outer surface.*—Color: Yellow-Green Group 144A with intonations of Greyed-Purple Group 183A at the apex. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—25 mm long, 8 mm wide.

*Receptacle.*—Texture: Smooth. Size: 8 mm in height, 7 mm wide. Color: Yellow-Green Group 144A. Shape: Campanulate.

*Pedicel.*—Surface: Smooth. Length: 50 mm. Diameter: 3 mm on average. Color: Yellow-Green Group 144A. Strength: Strong.

Flower bud development: Flower buds are borne in clusters of 5 to 7 flower buds per stem. Inflorescence are about 20 cm in diameter.

Flower bloom:

*Fragrance.*—Light floral.

*Duration.*—The blooms have a duration on the plant of approximately 14 days. Petals fall cleanly away from plant after flowers have fully matured.

*Size.*—Flower diameter is 90 mm when open. Flower depth is 35 mm.

*Flower shape.*—Open cup, double flower, with petals that curve out from the center.

*Shape of flower, side view.*—The upper portion is flat. The lower portion is convex.

Petalage: Under normal conditions, flowers have 50 petals total, 6 to 10 of which are petaloids.

General tonality of flower: Open flowers are Red-Purple Group 50A blended with Red-Purple Group 60B.

Petal color: Upon opening, outer petals Upper surface: Red-Purple Group 46A with intonations of Red-Purple Group 60B. Occasional streaks of White Group 155A. Lower surface: Red-Purple Group 60B. Upon opening, inner petals: Upper surface: Blend of Red-Purple Group 60A and 61B. Lower surface: Red-Purple Group 60B. Basal petal spots, upon opening: Upper surface: Yellow Group 13B. Lower surface: Yellow Group 13B. After opening, outer and inner petals Upper surface: Red-Purple Group 46A with intonations of Red-Purple Group 60B. Occasional streaks of White Group 155A. Lower surface: Red-Purple Group 60B. Basal petal spots, after opening: Upper surface: Yellow Group 13B. Lower surface: Yellow Group 13B.

Petals:

*Petal reflex.*—Somewhat reflexed.

*Margin.*—Entire and uniform. Occasionally a point at the center of the margin.

*Shape.*—Generally rounded. Apex shape: Rounded. Base shape: Obtuse.

*Size.*—45 mm (l)×45 mm (w).

*Texture.*—Smooth.

*Thickness.*—Average.

Petaloids:

*Size.*—15 mm (l) by 9 mm (w).

*Quantity.*—6 to 10.

*Shape.*—Acute base and rounded apex.

*Color.*—Upper surface is Blend of Red-Purple Group 60A and 61B. The lower surface is Red-Purple Group 60B. The basal zone is Yellow Group 13B.

Reproductive flower parts:

*Pollen.*—None observed.

*Anthers.*—Size: 2 mm in length. Color: Yellow Group 11A. Quantity: 40 on average.

*Filaments.*—Color: Greyed-Orange Group N163B. Length: 7 mm.

*Pistils.*—Length: 4 mm. Quantity: 15 on average.

*Stigmas.*—Color: Greyed-Yellow Group 160C.

*Styles.*—Color: Greyed-Yellow Group 160C.

*Hips.*—None observed to date.

Plant

Plant growth: Upright, bushy. Plants are 60 cm in height, and 50 cm wide.

Stems:

*Color.*—Juvenile growth: Yellow-Green Group 144B with intonations of Greyed-Orange Group 171A. Mature growth: Yellow-Green Group 152D.

*Length.*—On average, canes are 20 cm from the base of the plant to the flowering portion.

*Diameter.*—About 6 mm.

*Internodes.*—On mature canes about 40 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 6 mm.

*Shape.*—Upper portion is concave. Lower portion is concave.

*Color.*—Juvenile prickles: Greyed-Yellow Group 160B. Mature prickles: Greyed-Yellow Group 160B.

Plant foliage:

*Compound leaf.*—150 mm (l)×80 (w).

*Quantity.*—2 leaves per 10 cm of stem on average.

*Color of juvenile foliage.*—Upper side: Yellow-Green Group 146A. Lower side: Yellow-Green Group 146A. Anthocyanin: Greyed-Purple Group 187A.

*Color of mature foliage*.—Upper side: Yellow-Green Group 147A. Lower side: Yellow-Green Group 147B.

Plant leaves and leaflets:

*Stipules*.—Size: 21 mm long, 6 mm wide. Quantity: 2 per compound leaf. Shape: Linear, slightly broad based with outward extending apices. Margins: Finely serrated. Color: Yellow-Green Group 144B.

*Petiole*.—Length: 40 mm. Diameter: 1.5 mm.

*Upper surface*.—Color: Yellow-Green Group 144A.

*Lower surface*.—Color: Yellow-Green Group 144A with intonations of Greyed-Purple Group 183A.

*Rachis*.—Length: 50 mm. Upper surface: Color: Yellow-Green Group 144A.

*Lower surface*.—Color: Yellow-Green Group 144A with intonations of Greyed-Purple Group 183A.

*Leaflet*.—Quantity: Normally 5 to 7 leaflets. Margins: Serrated. Size: On average terminal leaflets are 60 mm long, 45 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa,* downy mildew *Peronospora sparsa,* rust *Phragmidium* sps., black spot *Diplocarpon rosae,* and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the Compact Floribunda rose class named 'Poulpal066', substantially as illustrated and described herein, due to its abundant red flowers, disease resistance, and extended period of bloom.

* * * * *

'Poulpal066'

'Poulpal066'